United States Patent
Jia et al.

(10) Patent No.: US 11,406,989 B2
(45) Date of Patent: Aug. 9, 2022

(54) APPARATUS AND METHODS CENTRIFUGAL AND MAGNETIC SAMPLE ISOLATION

(71) Applicant: ZYMO RESEARCH CORPORATION, Irvine, CA (US)

(72) Inventors: Xi-Yu Jia, Irvine, CA (US); Samuel Joseph Ollar, Irvine, CA (US)

(73) Assignee: ZYMO RESEARCH CORPORATION, Irvine, CA (US)

( * ) Notice: Subject to any disclaimer, the term of this patent is extended or adjusted under 35 U.S.C. 154(b) by 622 days.

(21) Appl. No.: 16/394,096

(22) Filed: Apr. 25, 2019

(65) Prior Publication Data

US 2019/0344287 A1  Nov. 14, 2019

Related U.S. Application Data

(60) Provisional application No. 62/662,404, filed on Apr. 25, 2018.

(51) Int. Cl.
*B03C 1/30* (2006.01)
*B03C 1/01* (2006.01)
(Continued)

(52) U.S. Cl.
CPC .................. *B03C 1/30* (2013.01); *B03C 1/01* (2013.01); *B03C 1/0332* (2013.01);
(Continued)

(58) Field of Classification Search
CPC ........... B03C 1/30; B03C 1/01; B03C 1/0332; B03C 1/0335; B03C 1/288; B03C 2201/18; B03C 2201/26; B03C 2201/22; B04B 5/0414; B04B 9/12; C12Q 1/6806; G01N 1/40; G01N 35/0098; G01N 2035/00495; G01N 2035/00564; C12N 15/1013
(Continued)

(56) References Cited

U.S. PATENT DOCUMENTS 5,019,272 A * 5/1991 Kurahashi ............. B03C 1/0332
                                                     210/695
5,591,062 A    1/1997 Hettinger
(Continued)

FOREIGN PATENT DOCUMENTS

WO  WO-2001049419 A1 *  7/2001  ............... B03C 1/00
WO  WO-2017041607 A1 *  3/2017  ............... G01N 1/34

OTHER PUBLICATIONS

"Lab Centrifuge Fidget Spinner," Instructables.com, retrieved from the internet: https://www.instructables.com/id/Lab-Centrifuge-Fidget-Spinner/, retrieved Jul. 29, 2019.
(Continued)

*Primary Examiner* — Nam X Nguyen
*Assistant Examiner* — Ekandra S. Miller-Cruz
(74) *Attorney, Agent, or Firm* — Parker Highlander PLLC

(57) ABSTRACT

Provided herein are devices and methods for sample isolation comprising a planar member configured to rotate around a bearing, and a plurality of apertures positioned at an angle to the planar member. Exemplary embodiments relate generally to the field of sample isolation, and more particularly to sample isolation using centrifugal and magnetic forces.

15 Claims, 14 Drawing Sheets

(51) Int. Cl.
*B04B 5/04* (2006.01)
*B03C 1/033* (2006.01)
*B03C 1/28* (2006.01)
*C12Q 1/6806* (2018.01)
*G01N 1/40* (2006.01)
*C12N 15/10* (2006.01)

(52) U.S. Cl.
CPC ............ *B03C 1/0335* (2013.01); *B03C 1/288* (2013.01); *B04B 5/0414* (2013.01); *C12Q 1/6806* (2013.01); *G01N 1/40* (2013.01); *B03C 2201/18* (2013.01); *B03C 2201/26* (2013.01); *C12N 15/1013* (2013.01)

(58) Field of Classification Search
USPC .......... 210/695; 422/72, 415, 506, 533, 548, 422/918
See application file for complete search history.

(56) References Cited

U.S. PATENT DOCUMENTS

| | | | | |
|---|---|---|---|---|
| 2003/0116506 | A1* | 6/2003 | Lane | C02F 1/38 210/695 |
| 2004/0234416 | A1* | 11/2004 | Shimoyama | B04B 5/0414 422/72 |
| 2007/0023326 | A1* | 2/2007 | Armstrong | B03C 1/30 209/39 |
| 2010/0227379 | A1* | 9/2010 | Wo | C12M 47/04 435/308.1 |
| 2016/0361725 | A1* | 12/2016 | Eves | B03C 1/32 |

OTHER PUBLICATIONS

Goldman, Torsten, "Fidget Spinner Centrifuge," <https://www.youtube.com/watch?v=ac7BLbCLz-0>, 2017.

* cited by examiner

APPARATUS AND METHODS CENTRIFUGAL AND MAGNETIC SAMPLE ISOLATION

CROSS-REFERENCE TO RELATED APPLICATION

This application claims priority to U.S. Provisional Patent Application 62/662,404 filed Apr. 25, 2018, the entire contents of which are incorporated herein by reference.

BACKGROUND OF THE INVENTION

1. Field of the Invention

The present invention relates generally to the field of sample isolation, and more particularly to sample isolation using centrifugal and magnetic forces.

2. Description of Related Art

Conventional sample isolation apparatus and methods utilizing magnetic or centrifugal forces suffer notable disadvantages, including those discussed below.

For example, typical magnetic separation devices (e.g. often referred to as magnetic stands or magnetic racks) are designed to hold a sample-containing tube in a vertical position with magnets vertically situated and parallel to the tube center axis. These traditional devices condense magnetic beads along the tube wall closest to the magnet. This configuration can be suitable for placing a pipette to the bottom of the tube to aspirate supernatant without aspirating magnetic beads. However, with this configuration, some supernatant remains on the beads due to surface tension. This remaining supernatant can cause contamination carry-over into the next step in the process and may affect the purity of the final eluate.

In addition, traditional centrifugation apparatus and methods result in the magnetic beads pelleting at the bottom of the centrifuge immersed in the supernatant. These approaches are less efficient than using the traditional magnetic separation devices. For example, the magnetic beads are likely to be aspirated when the supernatant is removed from the pellet. Accordingly, a portion of the sample will be lost during the aspiration process and will not be available for analysis.

SUMMARY OF THE INVENTION

Exemplary embodiments of the present disclosure combine both magnetic isolation and centrifugation in one device. This approach can improve the efficiency of sample isolation (e.g. magnetic bead DNA/RNA isolation) by allowing for less carry over of supernatant. This can further result in cleaner preparation and reduced tube handling.

Exemplary embodiments include a device for isolating a sample, where the device comprises: a planar member comprising an upper planar surface, a lower planar surface, a central portion and an outer portion; a bearing positioned in the central portion of the planar member; and a support member proximal to the central portion of the planar member. In certain embodiments, the bearing comprises a first bearing race and a second bearing race, where the first bearing race and second bearing race are configured to rotate with respect to each other; the planar member is coupled to the first bearing race of the bearing; the support member is coupled to the second bearing race of the bearing; the outer portion of the planar member comprises a plurality of apertures distal to the central portion; each aperture of the plurality of apertures extends through the planar member at an angle to the planar member, where the angle to the planar member is between 30 degrees and 50 degrees when measured from a central axis of the aperture to the upper planar surface between the aperture and the central portion; the outer portion of the planar member comprises a plurality of magnets positioned such that each magnet in the plurality of magnets is located between the bearing and an aperture in plurality of apertures; and the device is configured to allow rotation of the planar member around the support member.

In particular embodiments, the angle to the planar member is between 35 and 45 degrees, or more specifically between 37 and 41 degrees, or more specifically approximately 39 degrees. In some embodiments, each magnet of the plurality of magnets is inserted in the lower planar surface of the planar member. In specific embodiments, the plurality of magnets comprises 52 percent Neodymium. In certain embodiments, each aperture of the plurality of apertures is tapered such that each aperture is larger at the upper planar surface than the aperture is at the lower planar surface. In particular embodiments, each aperture of the plurality of apertures is configured such that each aperture is configured to receive a tubular member comprising a cylindrical upper portion and a tapered conical lower portion.

In some embodiments, each aperture is of the plurality of apertures configured such that substantially all of a surface of the planar member surrounding each aperture maintains contact with the tubular member when the tubular member is inserted into the aperture. In specific embodiments, a surface of the planar member surrounds each aperture; the surface of the planar member surrounding each aperture comprises a cylindrical portion proximal to the upper planar surface of the planar member; and the surface of the planar member surrounding each aperture comprises a tapered conical portion proximal to the lower planar surface of the planar member.

In certain embodiments, the planar member comprises a central axis at the center of the bearing; the surface of the planar member surrounding each aperture comprises an interface between the cylindrical portion and the tapered conical portion; and the point of the interface that is closest to the central axis is substantially equidistant from the upper planar surface and the lower planar surface. In particular embodiments, each aperture in the plurality of apertures comprises a central axis at the center of the aperture; the surface of the planar member surrounding each aperture comprises an interface between the cylindrical portion and the tapered conical portion; the interface intersects the upper planar surface at a first point and a second point; the central axis of the aperture extends through the upper planar surface at a third point; and the first point, the second point, and the third point are substantially collinear.

Certain embodiments further comprise a base member configured to engage the support member. In particular embodiments, the base member comprises a plurality of electromagnets. In some embodiments, the plurality of electromagnets are arranged in a circle. Specific embodiments further comprise a control system configured to activate and deactivate each electromagnet in the plurality of electromagnets. In certain embodiments, the control system is configured to simultaneously activate a number of electromagnets in the plurality of electromagnets, wherein the number of electromagnets simultaneously activated is equal to the number of magnets in the plurality of magnets of the planar member. In particular embodiments, the control system is configured to sequentially activate and deactivate the plurality of electromagnets in the circle. In some embodiments, the plurality of magnets in the planar member are in a first plane; the plurality of electromagnets are in a second plane; and the base member comprises an elevated central portion configured to engage the support member such that the first plane is separated from the second plane by a gap between 1.0 and 4.0 mm. In specific embodiments, the outer portion of the planar member comprises a plurality of arms extending from central portion. In certain embodiments, the plurality of arms comprises three arms. In particular embodiments, the support member extends through the bearing positioned in the central portion of the planar member. In some embodiments, the support member comprises a first portion and a second portion, where: the first portion is configured to couple to the second portion; and the first portion and the second portion are configured such that the support member extends through the bearing when the first portion is coupled to the second portion. In specific embodiments, the first portion and the second portion are configured to threadably couple to each other.

Exemplary embodiments include a method of isolating a sample, where the method comprises: placing a tubular member in an aperture of a device as described herein (including for example, the device of claim 1), where the tubular member comprises a sample including a liquid comprising macromolecules and a solid; rotating the planar member around the support member; and aspirating a portion of the liquid from the tubular member. In certain embodiments, the solid is a magnetic solid and wherein the magnetic solid adsorbs macromolecules and is retained by a magnet when the first and second portions of the liquid are aspirated. Particular embodiments, further comprise aspirating an initial portion of liquid from the tubular member prior to rotating the planar member around the support member.

Exemplary embodiments include a device for isolating a sample, where the device comprises: a planar member comprising a plurality of sides, an upper planar surface, a lower planar surface, a central portion and an outer portion; a bearing positioned in the central portion of the planar member; and a support member proximal to the central portion of the planar member, where: the bearing comprises a first bearing race and a second bearing race, wherein the first bearing race and second bearing race are configured to rotate with respect to each other; the planar member is coupled to the first bearing race of the bearing; the support member is coupled to the second bearing race of the bearing; the outer portion of the planar member is coupled to the central portion at each side of the planar member; the outer portion of the planar member is coupled to the central portion at an angle between 125 degrees and 145 degrees; the outer portion comprises a plurality of apertures at each side of the planar member; and the device is configured to allow rotation of the planar member around the support member.

In certain embodiments, the outer portion comprises eight apertures at each side of the planar member. In particular embodiments, the outer portion of the planar member is coupled to the central portion at an angle of approximately 135 degrees. Specific embodiments further comprise a base member, wherein: the base member comprises a plurality of sides equal to the number of sides of the planar member; and each side of the base member comprises a plurality of magnets equal to the number of apertures at each side of the planar member. In certain embodiments, the base member is configured to support the support member, the bearing and the planar member to allow rotation of the planar member with respect to the support member. In particular embodiments, the plurality of magnets comprises 52 percent Neodymium.

Exemplary embodiments include a method of isolating a sample, where the method comprises: placing a tubular member in an aperture of the device as described herein (including for example, the device of claim 1), where the tubular member comprises a sample including a liquid comprising macromolecules and a solid; rotating the planar member around the support member; and aspirating a portion of the liquid from the tubular member. In certain embodiments the solid is a magnetic solid and the magnetic solid adsorbs macromolecules and is retained by a magnet when the first and second portions of the liquid are aspirated. Particular embodiments further comprise aspirating an initial portion of liquid from the tubular member prior to rotating the planar member around the support member.

Exemplary embodiments include a device for isolating a sample, where the device comprises: a first three-sided planar member; the first three-sided member further comprising a centered opening for axial rotation around a shaft; each side of the three-sided members further comprising a rectangular planar member projecting at an angle from a side of the three-sided member configured with a plurality of circular openings for receiving microcentrifuge tubes or strips of connected microcentrifuge tubes; a second base member further comprising a raised shelf configured for receiving a rolling bearing, a circular base and a shelf and a shaft projecting from the base and shelf, wherein the shaft has external threading or another fastening means for allowing rotation of the first three-sided planar member by application of a torque (rotational force) by hand; a button comprising internal thread or for receiving the external thread of the shaft or another fastening means for securing the shaft; a bearing positioned in contact with the top of the shelf of the second base member and bottom of the first planar member; and an optional third riser member configured to mate with the top of the second base member and the bottom of the first three-sided member for elevating the second base member and first three-sided planar member from a surface providing for clearance for rotational motion of the first planar member's microfuge tubes or strips of connected microfuge tubes positioned in the plurality of circular openings of each of the rectangular planar member of the first three-sided member.

Exemplary embodiments include a modular biological sample isolation device comprising: a first three-sided planar member; the first three-sided member further comprising a centered opening for axial rotation around a shaft; each side of the three-sided members further comprising a rectangular planar member projecting at an angle from a side of the three-sided member configured with a plurality of circular openings for receiving microcentrifuge tubes or strips of connected microcentrifuge tubes; a second base member further comprising a raised shelf configured for receiving a rolling bearing, a circular base and a shelf and a shaft projecting from the base and shelf, wherein the shaft has external threading or another fastening means for allowing rotation of the first three-sided planar member by application of a torque (rotational force) by hand; a button comprising internal thread or for receiving the external thread of the shaft or another fastening means for securing the shaft; a bearing positioned in contact with the top of the shelf of the second base member and bottom of the first planar member; and an optional third riser member configured to mate with the top of the second base member and the bottom of the first three-sided member for elevating the second base member and first three-sided planar member from a surface providing for clearance for rotational motion of the first planar member's microfuge tubes or strips of connected microfuge tubes positioned in the plurality of circular openings of each of the rectangular planar member of the first three-sided member.

Exemplary embodiments include a modular biological sample isolation device comprising: a first planar member with a plurality of lobes further comprising a centered opening through the member relative to the axis of rotational motion for axial rotation around a shaft; each of the three lobes further comprising a centered and angled opening through the planar member for receiving a microcentrifuge tube so that the microcentrifuge tube is seated in the opening at an angle; a magnet positioned into the first planar member on the side of the centered or off-set opening for axial rotation and adjacent to the opening for receiving a microcentrifuge tube on each of the lobes so that the magnetic force is exerted across the microcentrifuge tube's diameter; a second base member further comprising a raised shelf configured for receiving a rolling bearing, a circular base and a shaft projecting from the base, wherein the shaft has external threading or another fastening means for allowing rotation of the first three-sided planar member by application of a torque or rotational force by hand; a button member comprising internal thread or for receiving the external thread of the shaft or another fastening means for securing the shaft and for providing a surface for application of a torque or rotational force by hand; a bearing positioned in contact with the top of the shelf of the second base member and bottom of the first planar member; and a riser member for elevating the second base member and first three-sided planar member from a surface providing for clearance for rotational motion of the first planar member's microfuge tubes or strips of connected microfuge tubes positioned in the plurality of circular openings of each of the rectangular planar member of the first three-sided member.

Certain embodiments further comprise a magnetic base. In particular embodiments, the centered opening is about 10 mm to about 22 mm. In specific embodiments, the members are made of a material selected from the group consisting of printed or molded plastic or other polymer, wood, and metal. In certain embodiments, the bearing is selected from the group consisting of a rolling element bearing, a magnetic bearing, a jewel bearing, a fluid bearing, a flexure bearing, and a plurality of plain bearings. In particular embodiments, the plurality of openings of the rectangular planar member is eight openings. In some embodiments, the diameter of the openings is about 7 mm and the spacing between openings is about 2.2.mm. In specific embodiments, the rectangular planar member is angled at about 45° relative to the planar ember surface. In certain embodiments, the first planar member is about 3.5 to about 7.0 mm in thickness. In particular embodiments, the second member is round with a diameter of about 45 mm and a thickness of about 3.5 to about 7.0 mm. In some embodiments, the shelf of the second base member is about 12 mm is diameter and the shaft is about 8 mm in diameter. In specific embodiments, the shaft is about 5.5 mm to about 9.0 mm in height from the upper surface of the second member. In certain embodiments, the torque or rotational force is applied by hand or via other mechanical or electronical means for providing torque or rotational force.

Using exemplary embodiments of the present disclosure (sometimes referred to herein by the commercial name "Fuge-It"), excess supernatant that is held to the magnetic beads can be removed via centrifugation. This can be accomplished without disturbing the placement of the magnetic bead pellet, allowing the user to aspirate remaining supernatant, thereby reducing the amount of carryover between steps.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about", "approximately" or related terms are used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. In addition.

DESCRIPTION OF ILLUSTRATIVE EMBODIMENTS

Figure 1:
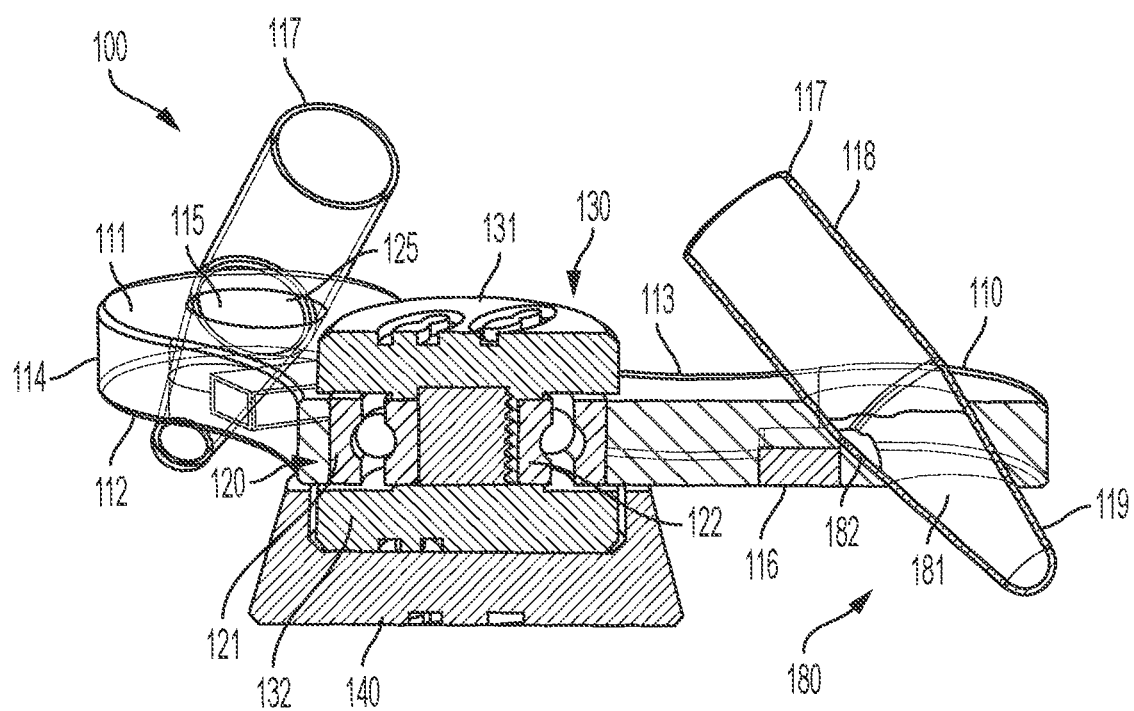
FIG. 1 illustrates a partial cross-section view of a device for sample separation according to an exemplary embodiment of the present disclosure at an initial step during operation.

Referring initially to FIGS. 1-3 and FIGS. 8-10, partial section views are shown illustrating a device 100 for isolating a sample during use. Additional views of specific components of device 100 are shown in FIGS. 4-9. In this embodiment, device 100 comprises a planar member 110 comprising an upper planar surface 111, a lower planar surface 112, a central portion 113 and an outer portion 114. In addition, device 100 comprises a bearing 120 positioned in central portion 113 of planar member 110. Device 100 further comprises a support member 130 proximal to central portion 113 of planar member 110. In the embodiment shown, bearing 120 comprises a first bearing race 121 and a second bearing race 122 configured to rotate with respect to each other. Planar member 110 is coupled to first bearing race 121 and second bearing race 122 is coupled to support member 130 in the illustrated embodiment.

In the embodiment shown, device 100 also comprises a base member 140 configured to engage support member 130. It is understood that other embodiments may not comprise a base member to engage support member 130. For example, in certain embodiments a user can place support member 130 between his or her thumb and a finger to support device 100 and allow planar member 110 to rotate around bearing 120. In the embodiment shown, support member 130 comprises a first portion 131 and a second portion 132 that are threadably coupled, such that support member 130 extends through bearing 120 when first portion 131 is coupled to second portion 132.

In this embodiment, outer portion 114 of planar member 110 comprises a plurality of apertures 115 distal to central portion 113. Outer portion 114 also comprises a plurality of magnets 116 positioned such that each magnet 116 is located between bearing 120 and an aperture 115. Each aperture 115 can be tapered such that it is larger at upper planar surface 111 than the aperture is at lower planar surface 112. In particular embodiments each aperture 115 can be configured to receive a tubular member 117 comprising a cylindrical upper portion 118 and a tapered conical lower portion 119. As explained further below, tubular member 117 can be a microcentrifuge tube 117 (e.g. sometimes commonly referred to as an Eppendorf tube) to allow isolation of a sample contained within the tube when planar member is rapidly rotated about bearing 120.

In the embodiment shown, each aperture 115 extends through planar member 110 at an angle A (shown in FIG. 6) to planar member 110 between 30 degrees and 50 degrees (when angle A is measured from a central axis 105 of aperture 115 to upper planar surface 111 between aperture 115 and central portion 113). In certain embodiments, Angle A may be between 35 and 45 degrees, or more particularly between 37 and 41 degrees. In the particular embodiment shown, angle A is approximately 39 degrees. In this embodiment, each aperture 115 is configured such that substantially all of a surface 125 of planar member 110 surrounding each aperture 115 maintains contact with tubular member 117 when tubular member 117 is inserted into aperture 115. Surface 125 may comprise a cylindrical portion 126 proximal to upper planar surface 111 and a tapered conical portion 127 proximal to lower planar surface 112, with an interface 128 between cylindrical portion 126 and tapered conical portion 127.

Figure 4:
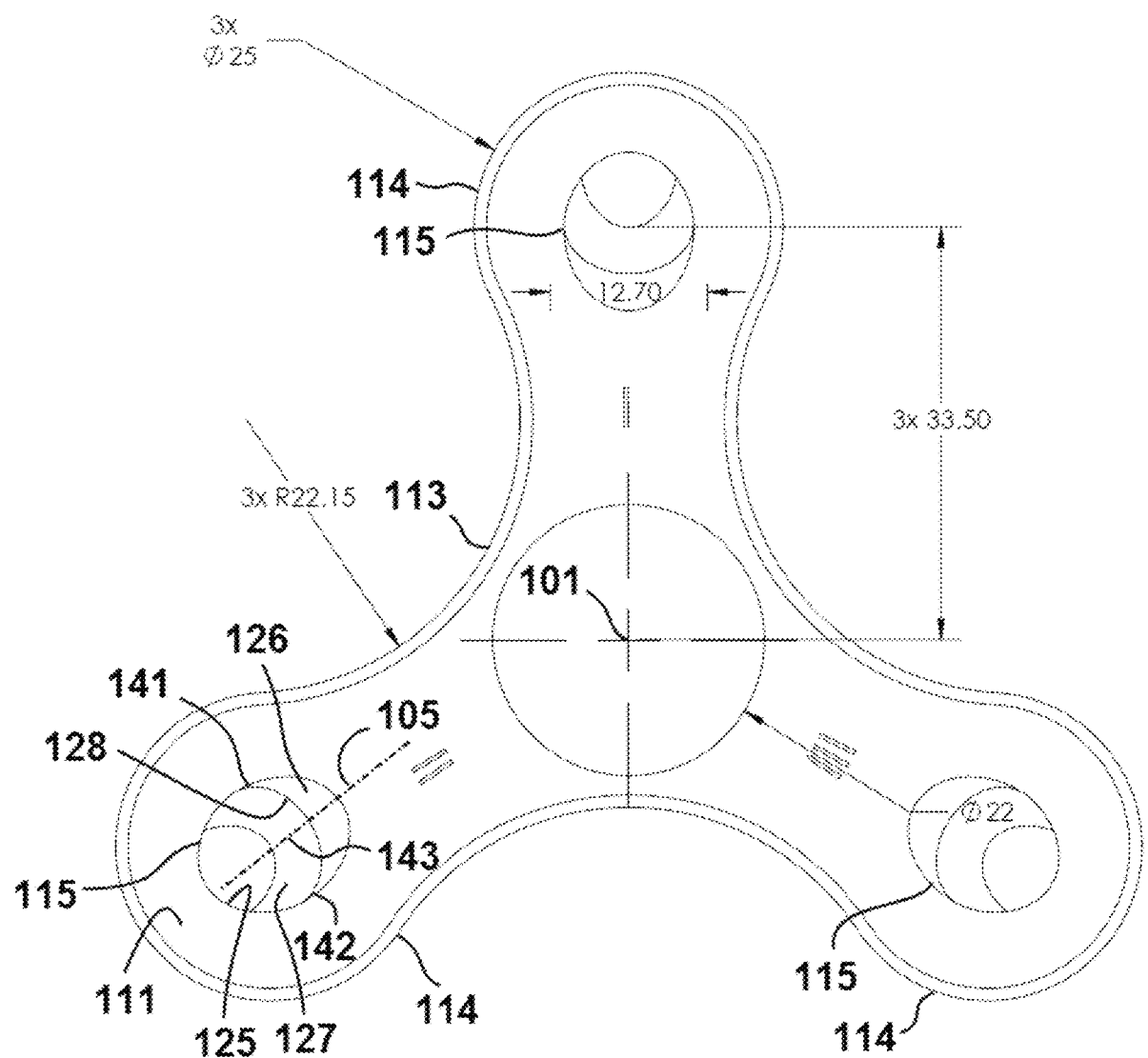
FIG. 4 illustrates a top view of a planar member of the embodiment of FIG. 1.
Figure 5:
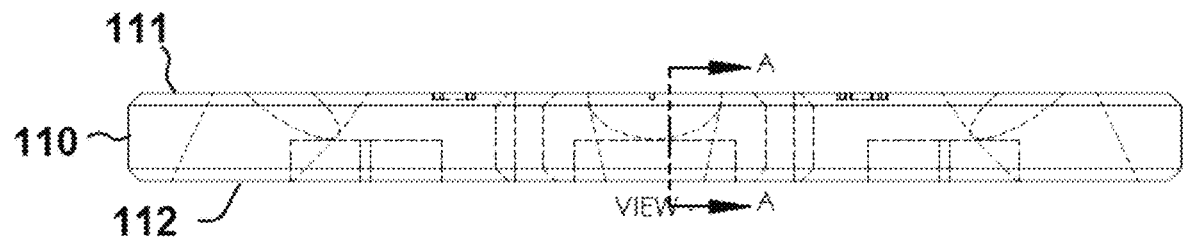
FIG. 5 illustrates a side view of the planar member of FIG. 4.
Figure 6:
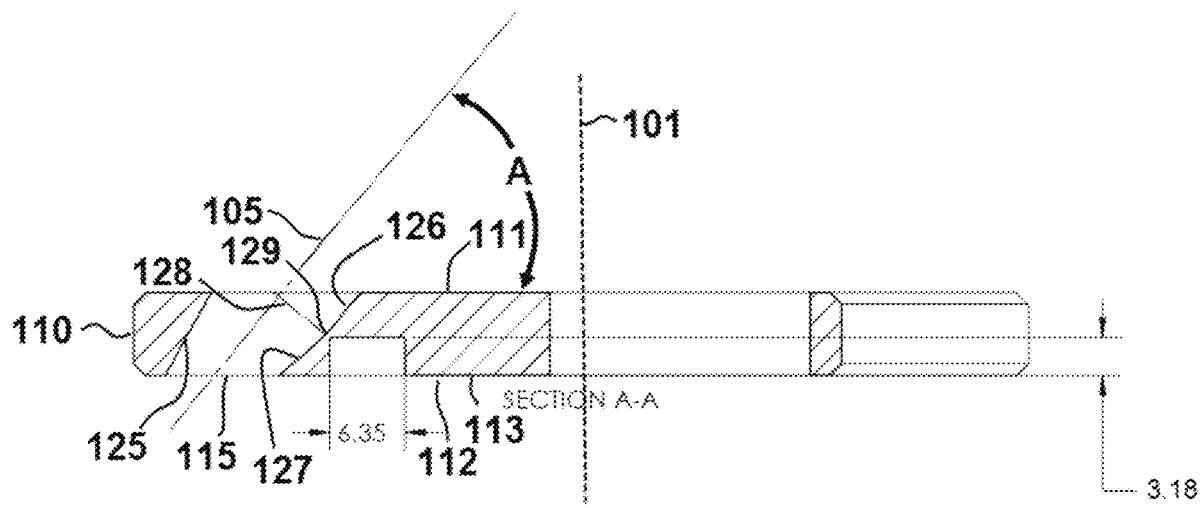
FIG. 6 illustrates a section view taken along line A-A of FIG. 5.
Figure 7:
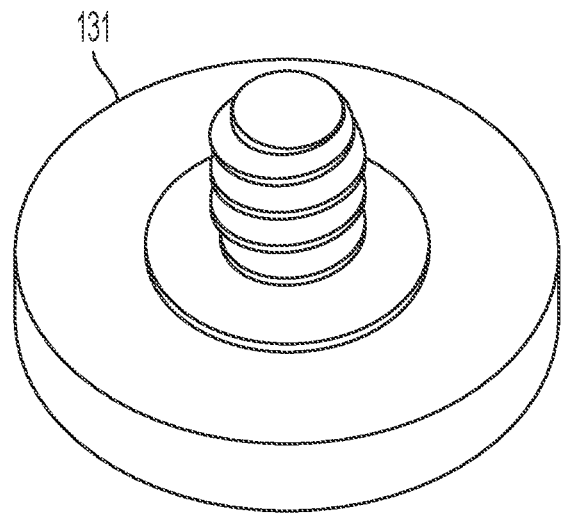
FIG. 7 illustrates a perspective view of a first portion of a support member of the embodiment of FIG. 1.
Figure 8:
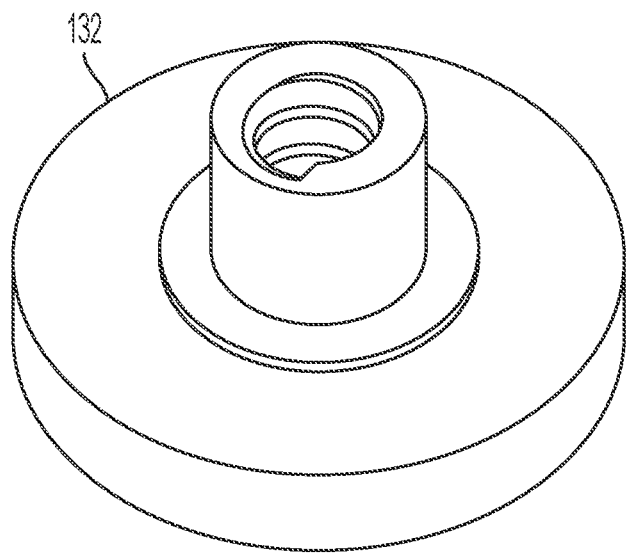
FIG. 8 illustrates a perspective view of a second portion of a support member of the embodiment of FIG. 1
Figure 9:
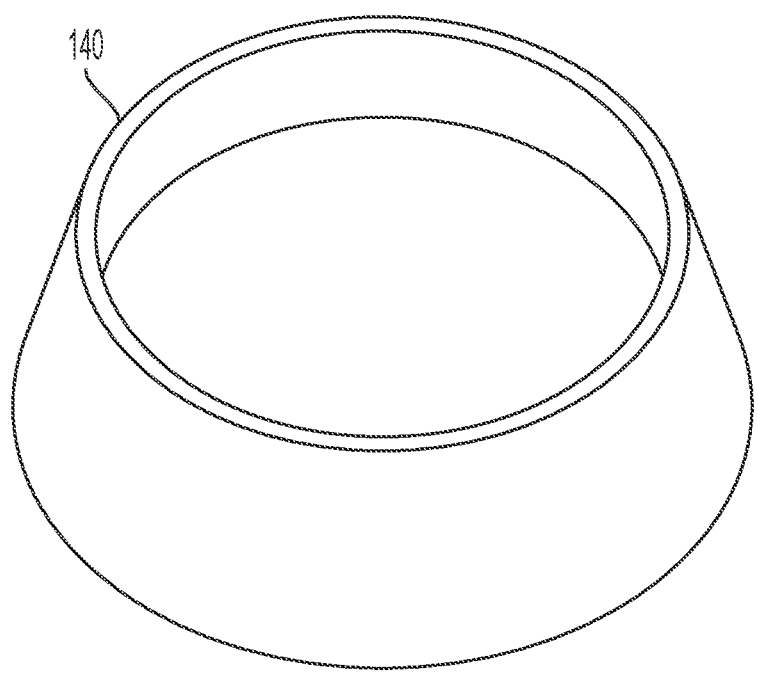
FIG. 9 illustrates a perspective view of a base member of the embodiment of FIG. 1.

As shown in FIG. 6, a point 129 of interface 128 that is closest to a central axis 101 (at center of bearing 120) is substantially equidistant from upper planar surface 111 and lower planar surface 112. As shown in FIG. 4 and FIG. 5 (planar view of FIG. 4), interface 128 intersects upper planar surface 111 at a first point 141 and a second point 142, while central axis 105 extends through upper planar surface 111 at a third point 143. In the embodiment shown, first point 141, second point 142, and third point 143 are substantially collinear.

Figure 2:
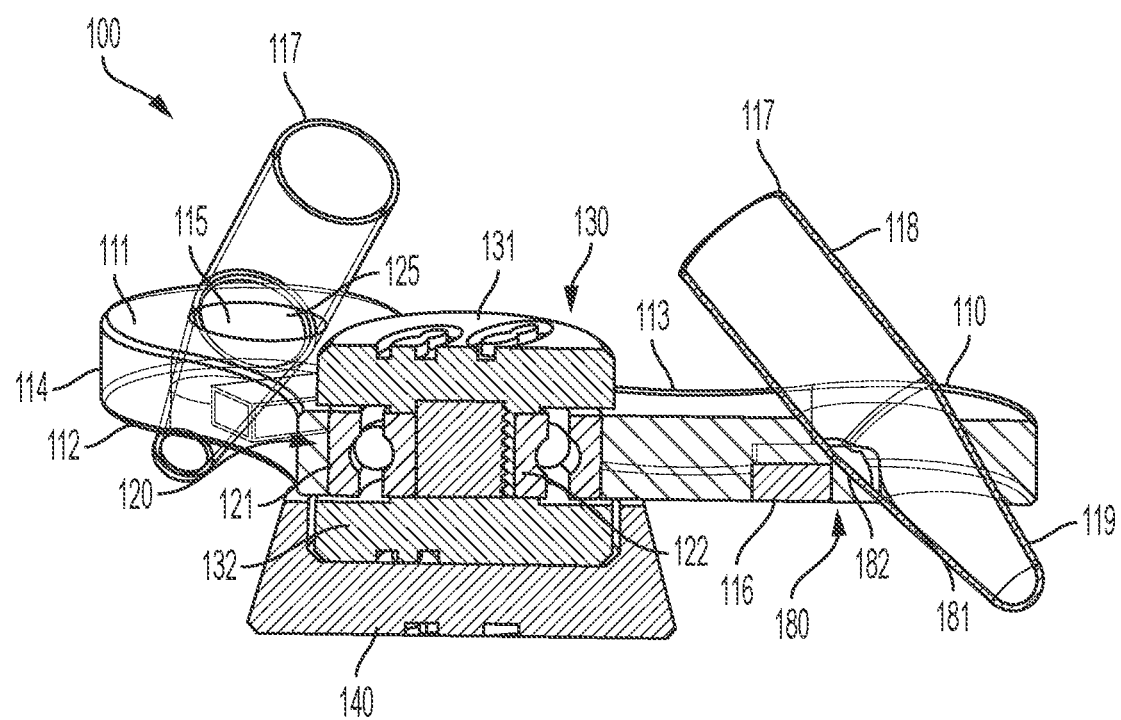
FIG. 2 illustrates a partial cross-section view of the embodiment of FIG. 1 during a subsequent step of operation.
Figure 3:
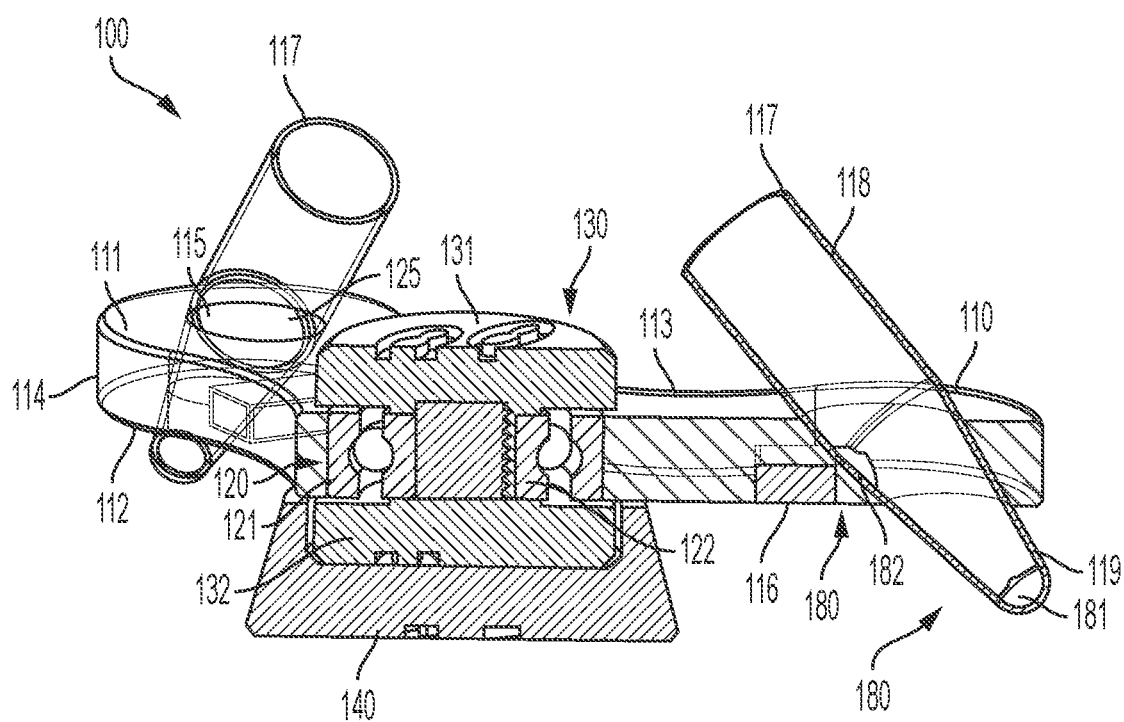
FIG. 3 illustrates a partial cross-section view of the embodiment of FIG. 1 during a subsequent step of operation.

As shown in FIG. 1-3, during operation of device 100, a tubular member 117 comprising a sample 180 can be placed in each aperture 115. In the embodiment shown, sample 180 comprises a liquid 181 (e.g. a supernatant) and a solid 182 (e.g. a solid including magnetic beads). After placing tubular members 117 into apertures 115, solid 182 will be attracted to magnet 116, while liquid 181 will collect in the tapered conical portion 127 of tubular member 117. This can allow a user to aspirate a majority of liquid 181 from tubular member 117. In order to remove additional liquid 181 that may remain on solid 182, a user can then rotate planar member 110 to provide a centrifugal effect to the contents of tubular members 117. This process can be used, for example, to allow a user to isolate macromolecules such as genetic material from a solution using magnetic isolation beads (e.g. for DNA/RNA or protein). In certain embodiments, only a single aspiration step may be needed after the centrifuge step (e.g. if a minimal amount of liquid is present in tubular member 117). In other embodiments, at least two aspiration steps may be needed after the centrifuge step (e.g. to remove residual amounts of liquid often present in sample 180 of tubular member 117).

The angle at which tubular members 117 are positioned with respect to planar member 110 directs liquid 181 away from solid 182 and to the bottom of tapered conical portion 127. The remaining liquid 181 can then be aspirated from tubular members 117. While the above description provides an overview of the operation of device 100, a specific example of a particular protocol is provided in the working example described below.

The angle, depth, and placement of the apertures 115 (and consequently tubular members 117) relative to magnet 116 are configured to provide optimal magnetic force on solid 182 comprising adsorbed macromolecules. This configuration also provides for a placement of solid 182 within tubular member 117 a distance from the bottom of tapered conical portion 127 sufficient to clear solid 182 of excess liquids spun down during centrifugation. Furthermore, the configuration ensures tubular member 117 remain seated apertures 115 when planar member 110 is rotate around bearing 120. Combining magnetic bead isolation with centrifugation facilitates improved supernatant removal, resulting in less carryover contaminants, resulting in cleaner eluates.

Figure 10:
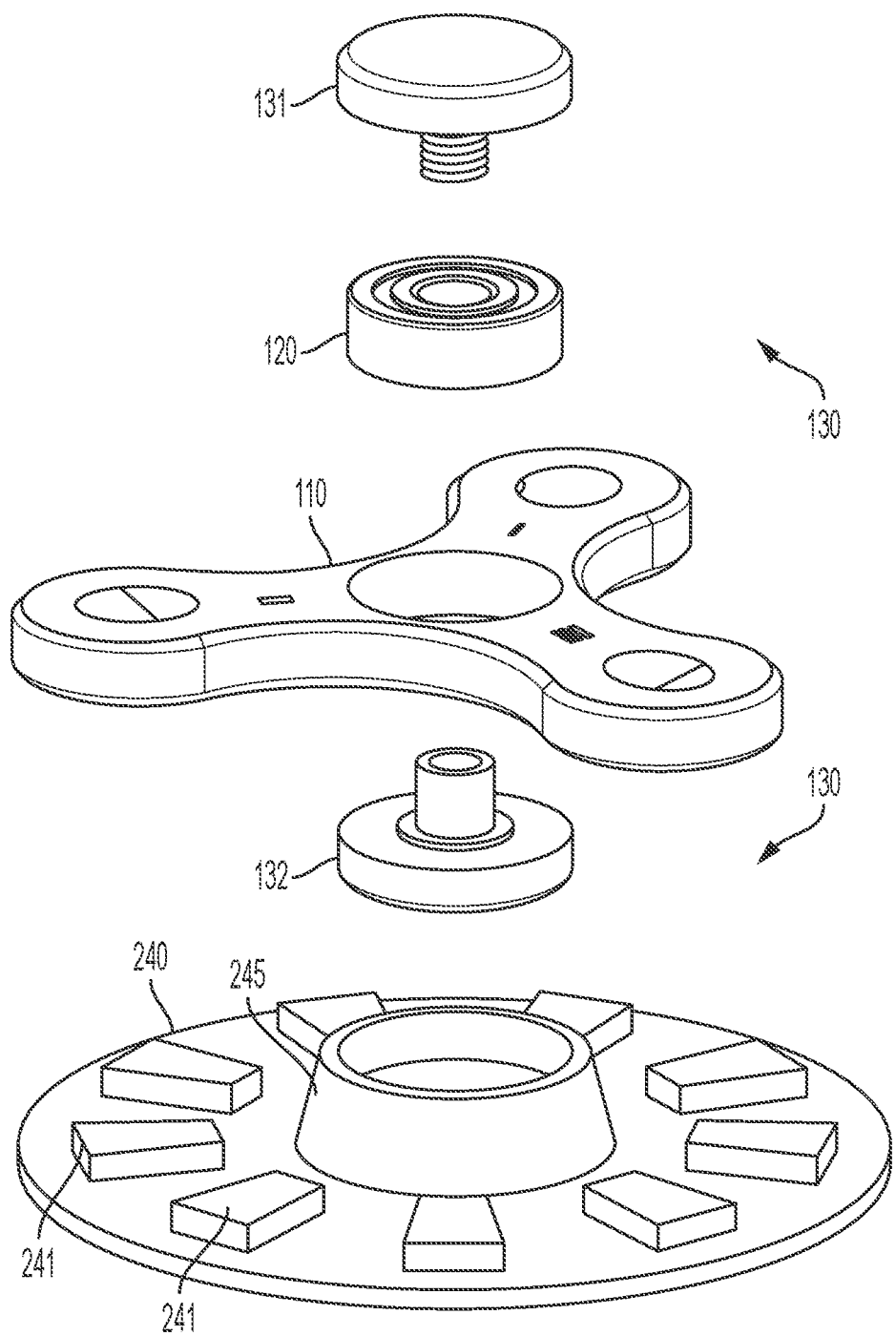
FIG. 10 illustrates an exploded view of a device for sample separation according to an exemplary embodiment of the present disclosure.
Figure 11:
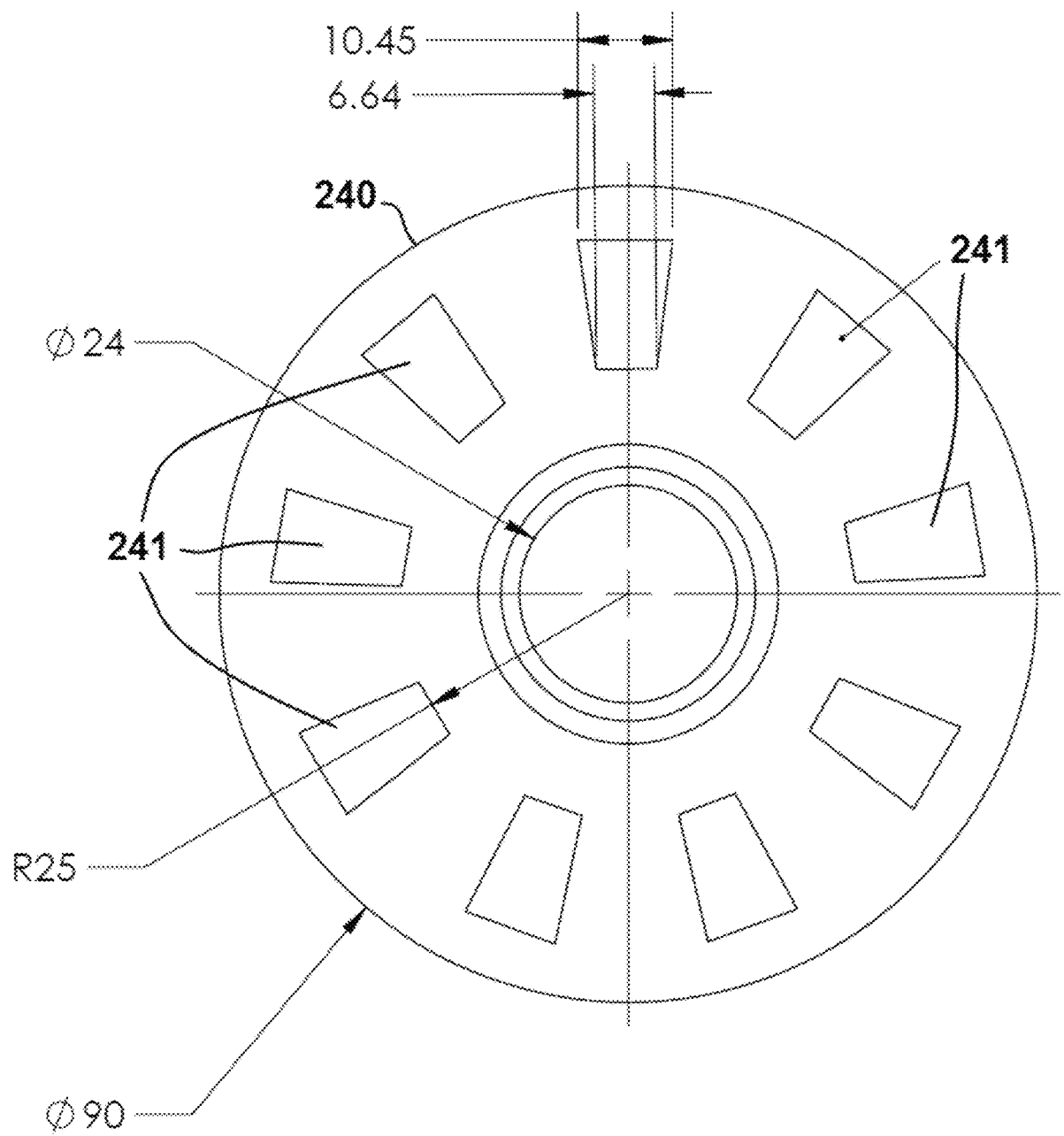
FIG. 11 illustrates a top view of a base member of the embodiment of FIG. 10.
Figure 12:
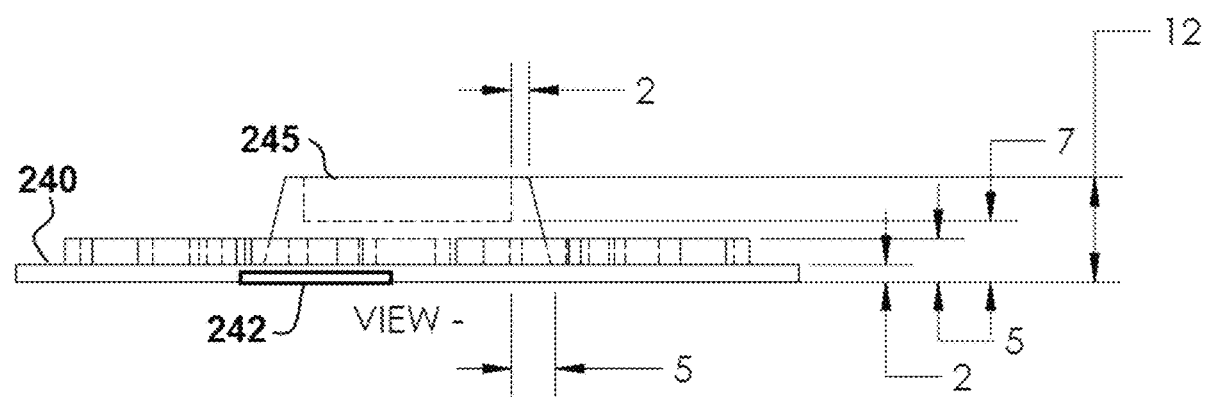
FIG. 12 illustrates a side view of the base member of FIG. 11.

Referring now to FIGS. 10-12, an embodiment is shown that is similar to the previously described embodiment but includes a different configuration for the base member. In this embodiment, base member 240 comprises a plurality of electromagnets 241 arranged in a circle. In particular embodiments, base member 240 comprises an elevated central portion 245 configured to engage support member 130 so that a plane containing electromagnets 241 is separated from a plane containing magnets 116 by a gap of between 1.0 and 4.0 mm.

Referring also to FIG. 1-3 as well, certain embodiments may further comprise a control system 242 (shown in FIG. 12) configured to activate and deactivate each electromagnet 241. Control system 242 (FIG. 12) can be configured to simultaneously activate a number of electromagnets 241. In specific embodiments, the number of electromagnets 241 simultaneously activated is equal to the number of magnets 116 in planar member 110 (e.g. three magnets in the embodiment shown). In some embodiments, control system 242 is configured to sequentially activate and deactivate electromagnets 241 in the circle. Magnets 116 and electromagnets 241 can be configured such that the electromagnets 241 can sequentially attract and repel magnets 116 as planar member 110 rotates. For example, an electromagnet 241 can be powered to attract a magnet 116 as the magnet approaches during rotation, and then electromagnet 241 can be powered to repel magnet 116 as magnet 116 moves away from electromagnet 241 (e.g. the current to electromagnet 241 can be reversed after magnet 116 passes over electromagnet 241 during rotation).

Referring also to FIG. 1-3 as well, in certain embodiments, the number of electromagnets 241 is an integer multiple of the number of magnets 116 (e.g. nine electromagnets 241 and three magnets 116 in the embodiment shown). This can allow a fraction of the electromagnets 241 to be powered at a given time (e.g. the number of electromagnets 241 powered simultaneously can correspond to the number of magnets 116) to drive planar member 110 during rotation. For example, in the embodiment shown, every third electromagnet 241 can be powered to initially attract a magnet 116 as the magnet approaches the electromagnet, and then powered to repel the magnet as the magnet moves away from the electromagnet. The initial set of powered electromagnets 241 can then be deactivated and each adjacent electromagnet 241 can then be powered, such that every third electromagnet 241 is then activated. This process can be repeated to provide a motivating force to rotate planar member 110. It is understood that in certain embodiments a user may provide an initial force to begin rotation of planar member 110. In addition, the device may comprise sensors to detect the relative position between planar member 110 and base member 240.

In this embodiment, magnets 116 serve a dual purpose. As previously described, magnets 116 can be used to separate a magnetic solid from a liquid (e.g. to isolate genetic material from a solution using magnetic isolation beads (e.g. for DNA/RNA or protein). In addition, magnets 116 can be used to rotate planar member 110 by coupling it with base member 240 and utilizing electromagnets 241 to direct the magnets around bearing 120.

Referring now to FIGS. 13-17 another embodiment of a device 300 for isolating a sample during use is illustrated. To avoid repetition, certain aspects of device 300 that are equivalent to previously described embodiments will not be repeated in the discussion of device 300. In addition, reference numbers that are similar to reference numbers of previous embodiments will be used to identify similar aspects or components (e.g. planar member 310 comprises an upper planar surface 311, a lower planar surface 312, a central portion 313 and an outer portion 314 where the previous embodiment incorporated a planar member 110 with upper planar surface 111, lower planar surface 112, a central portion 113 and an outer portion 114). Not all reference numbers shown in FIGS. 13-17 will be discussed herein, but it is understood that similar reference numbers correlate to similar aspects of the previous embodiments.

Figure 13:
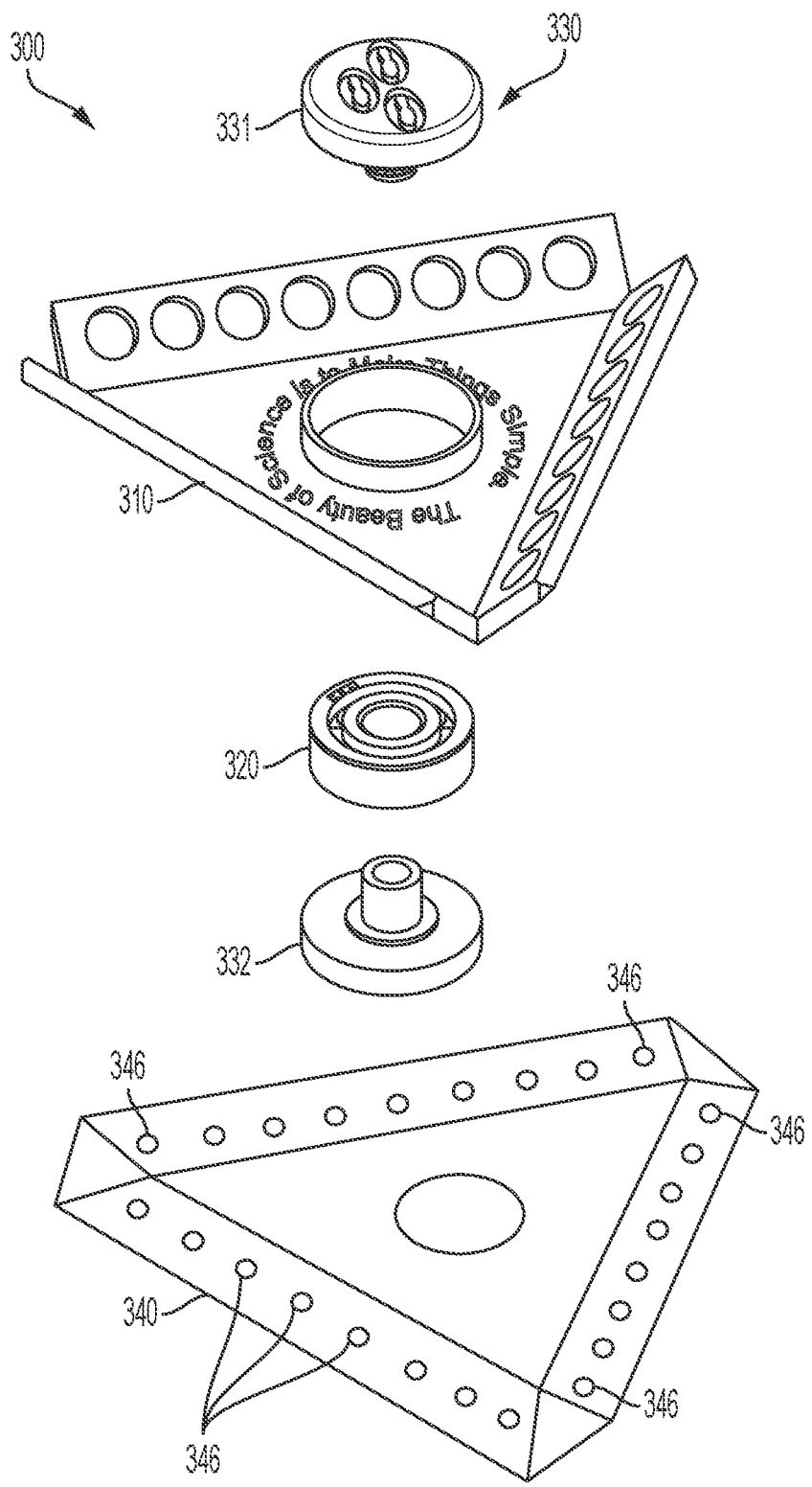
FIG. 13 illustrates an exploded view of a device for sample separation according to an exemplary embodiment of the present disclosure.
Figure 14:
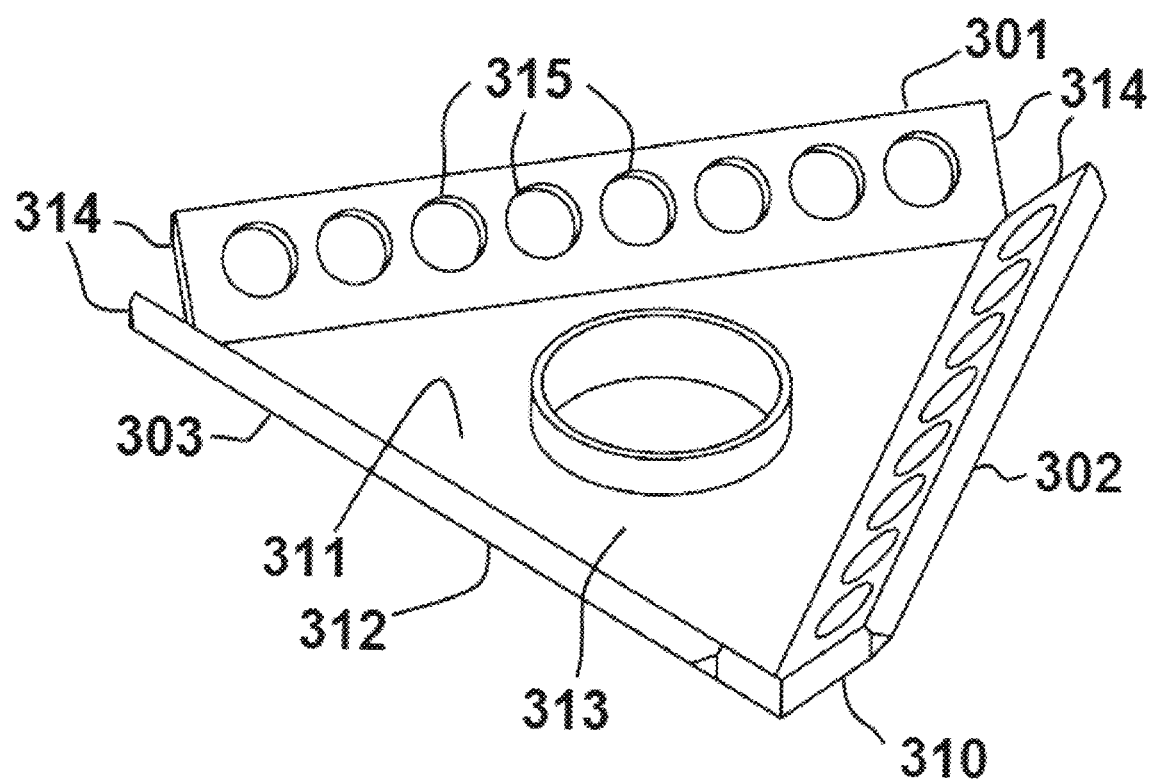
FIG. 14 illustrates a perspective view of the planar member of the embodiment of FIG. 13.
Figure 15:
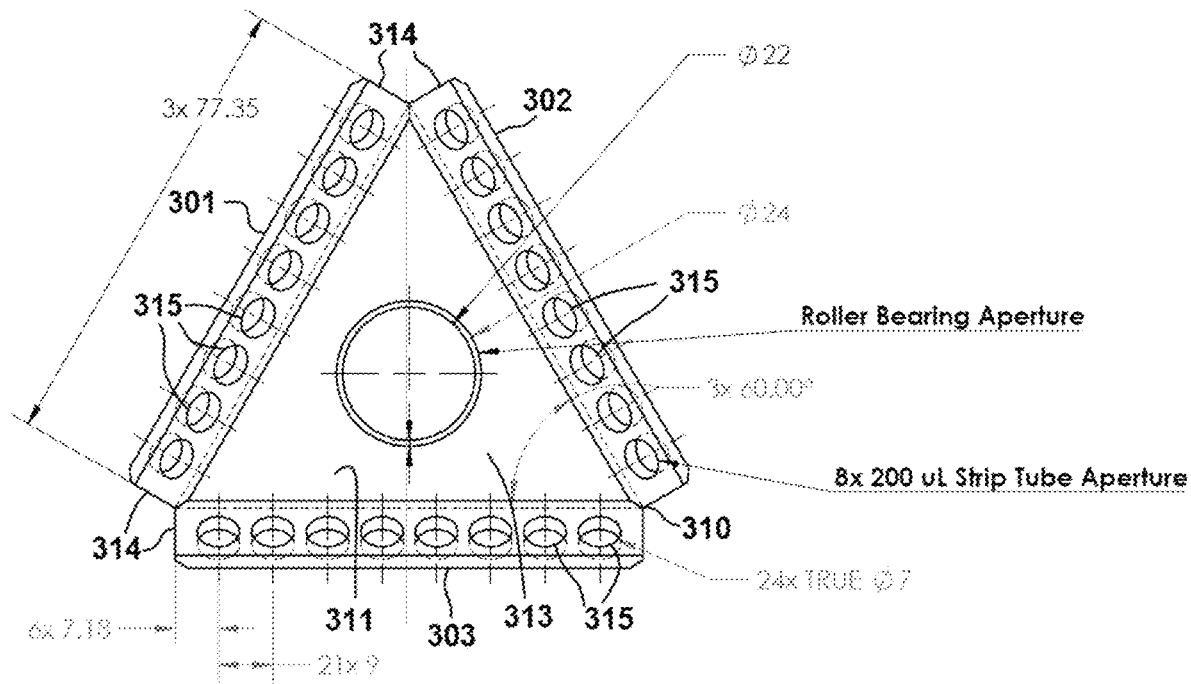
FIG. 15 illustrates a top view of the planar member of FIG. 14.
Figure 16:
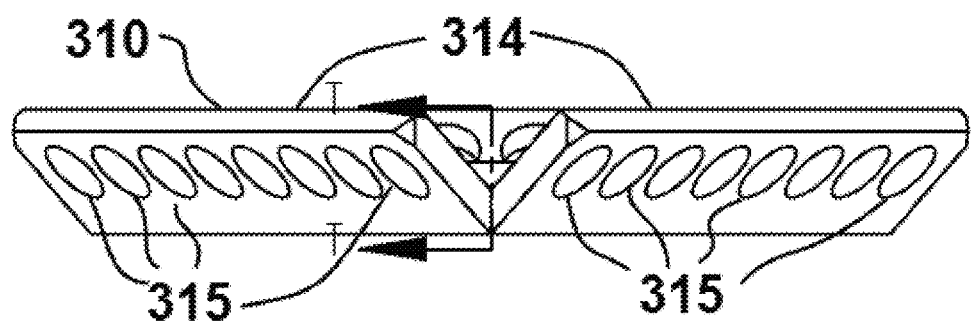
FIG. 16 illustrates a side view of the planar member of FIG. 14

In this embodiment, a planar member 310 is shown that can accommodate an increased number of cylindrical tubes for sample isolation. Planar member 310 operates in generally an equivalent manner to that of planar member 110. An exploded view of device 300 is shown in FIG. 13, followed by views of individual components in the following figures. In the embodiment shown, planar member 310 does not include magnets. Instead, a base member 340 includes a plurality of magnets 346. In the embodiment shown, device 300 also comprises a bearing 320 and a support member 330 comprising a first portion 331 and a second portion 332. Planar member 310 further comprises a central portion 313 configured to receive bearing 320 and an outer portion 314 with a plurality of apertures 315 configured to receive tubular members (not shown) in a manner similar to that of the previously described embodiments.

Figure 17:
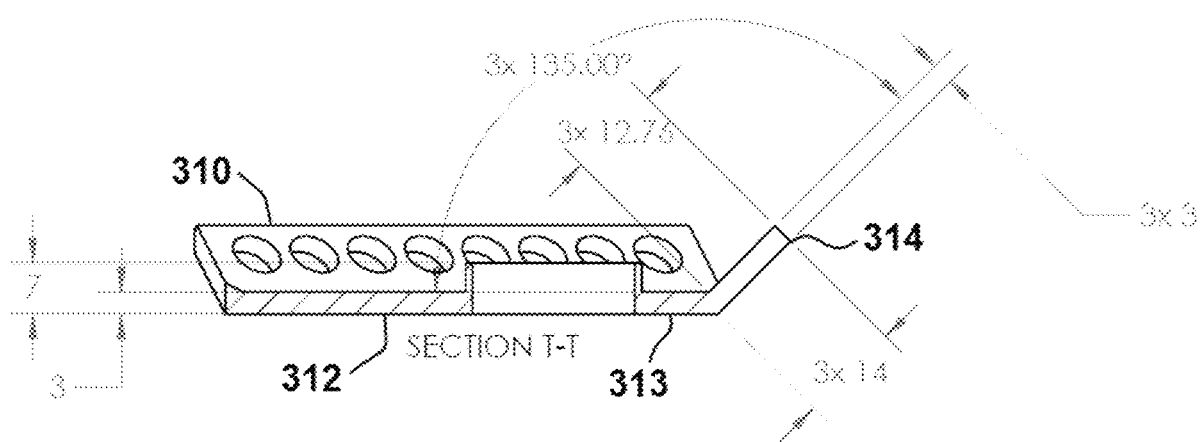
FIG. 17 illustrates a section view taken along line T-T of FIG. 16.

In the embodiment shown, bearing 320 and support member 330 are equivalent to previously described bearing 120 and support member 130 of the previously described embodiment. While planar member 310 is shown to comprise a plurality of three sides 301, 302 and 303 in this embodiment, it is understood that other embodiments may include a different number of sides. In the illustrated embodiment, each side of outer portion 314 is configured at an angle of 135 degrees to central portion 313 (as shown in FIG. 17). In other embodiments, outer portion 314 may be angled between 125 degrees and 145 degrees to central portion 313.

Device 300 can be operated in a manner similar to the previously described embodiment. For example, a user can place tubular members comprising samples in apertures 315. With tubular members placed in apertures 315, the user can then place support member 330 on base member 340 and rotate planar member 310 with the tubular members. It is understood that in certain embodiments, a user can support member 330 in other manners (e.g. between his or her thumb and a finger) rather than place planar member 310 on base member 340 to support device planar member 310 and allow planar member 310 to rotate around bearing 320. Outer portion 314 is angled with respect to central portion 313 so that the tubular members are held at an angle to central portion 313 (similar to the previously described embodiment). As planar member 310 and the tubular members are rapidly rotated around bearing 320, the centrifugal force can cause samples in the tubular members to separate liquids from solids. After the centrifugal force has been applied and the samples separated, the user can then align planar member 310 to base member 340 so that each aperture 315 is aligned with a magnet 346 in base member 340. The user can then aspirate liquids from the samples to prepare the samples for further processing and analysis.

In certain embodiments, a user can also perform an initial aspiration step prior to the centrifuge step. For example, a user can initially align the planar member 310 to base member 340 (prior to centrifuging) so that each aperture 315 is aligned with a magnet 346 in base member 340. The user can then aspirate a portion of fluid from the sample while magnets 346 retain the magnetic solids. The centrifuging and secondary aspiration can then be conducted as described above.

A particular example of a working protocol is provided below incorporating embodiments described herein. In certain steps of the protocol, exemplary embodiments of the devices may be referred to by their trade or commercial names (e.g. "Fuge-It").

Working Protocol:
For samples stored in DNA/RNA Shield
1 Add 100 µl of sample to DNase/RNase-free 1.7 mL microcentrifuge tube.
2 Add 2 µl Proteinase K enzyme (20 µg/µl stock) per 100 µl sample volume (final concentration 0.2% (v/v)).
3 Add 1000 µl of Viral DNA/RNA Buffer and mix per 100 µl of original sample volume.
　3.1 Bring total volume to 1200 µl with DNA/RNA Shield
4 Add 20 µl Magbinding Beads per 100 µl of original sample volume.
5 Mix samples well and vortex (~1,300 rpm) for 20 minutes at room temperature.
6 Place sample tubes in Fuge-It*
　6.1 Place Fuge-It on its base, secure it by pressing down on the top button
　6.2 Spin down any fluid stuck in the cap or on the sides of the tube
　6.3 Allow to stand for at least 30 seconds to pellet Magnetic Binding Beads
　6.4 Aspirate supernatant.
　6.5 Spin Fuge-It to remove excess supernatant from pellet
　6.6 Aspirate remaining supernatant
7 Wash 1:
　7.1 Remove microcentrifuge tube from Fuge-It and mix Magbinding Beads with 500 µl Magbead Wash 1.
　7.2 Transfer Magbinding bead-wash solution to a new 1.7 mL microcentrifuge tube and repeat Step 6.
8 Wash 2:
　8.1 Remove microcentrifuge tube from Fuge-It and mix Magbinding Beads with 500 µl Magbead Wash 2.
　8.2 Repeat Step 6.
9 Wash 3:
　9.1 Remove microcentrifuge tube from Fuge-It and mix Magbinding Beads with 500 µl 95% ethanol.
　9.2 Transfer Magbinding bead-wash solution to a new 1.7 mL microcentrifuge tube
　9.3 Repeat Step 6
　9.4 Following aspiration of supernatant, spin tubes to pull remaining ethanol from the beads
　9.5 Aspirate remaining supernatant
10 Heat the Magbinding Beads on a hot plate for 10-15 minutes at 65° C. to dry, or until they no longer appear glossy
11 Suspend beads in 30 µl DNase/RNase-Free Water for every 100 µl of original sample.
　11.1 Place samples in Fuge-It
　11.2 Pipette to eluate/Magbead solution directly onto the tube wall directly over the magnet
　11.3 Allow to stand >30 second
　11.4 Spin Fuge-It to remove eluate from pellet
　11.5 Transfer eluate to a new DNase/RNase free tube.

All of the devices and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. No. 5,591,062

What is claimed is:
1. A device for isolating a sample, the device comprising: a planar member comprising an upper planar surface, a lower planar surface, a central portion and an outer portion; a bearing positioned in the central portion of the planar member; and a support member proximal to the central portion of the planar member, wherein: the bearing comprises a first bearing race and a second bearing race, wherein the first bearing race and the second bearing race are configured to rotate with respect to each other; the planar member is coupled to the first bearing race of the bearing; the support member is coupled to the second bearing race of the bearing; the outer portion of the planar member comprises a plurality of apertures distal to the central portion; each aperture of the plurality of apertures extends through the planar member at an angle to the planar member, wherein the angle to the planar member is between 30 degrees and 50 degrees when measured from a central axis of the aperture to the upper planar surface between the aperture and the central portion; the outer portion of the planar member comprises a plurality of magnets positioned such that each magnet in the plurality of magnets is located between the bearing and the aperture in the plurality of apertures; and the device is configured to allow rotation of the planar member around the support member.

2. The device of claim 1 wherein the angle to the planar member is between 35 and 45 degrees.

3. The device of claim 1 wherein the angle to the planar member is between 37 and 41 degrees.

4. The device of claim 1 wherein the angle to the planar member is approximately 39 degrees and each magnet of the plurality of magnets is inserted in the lower planar surface of the planar member.

5. The device of claim 1 wherein the plurality of magnets comprises 52 percent Neodymium.

6. The device of claim 1 wherein each aperture of the plurality of apertures is i) tapered such that each aperture is larger at the upper planar surface than the aperture is at the lower planar surface; ii) configured such that each aperture is configured to receive a tubular member comprising a cylindrical upper portion and a tapered conical lower portion; and iii) configured such that substantially all of a surface of the planar member surrounding each aperture maintains contact with the tubular member when the tubular member is inserted into the aperture.

7. The device of claim 1 wherein: the device further comprises a base member configured to engage the support member; the base member comprises a plurality of electromagnets arranged in a circle; the plurality of magnets in the planar member are in a first plane; the plurality of electromagnets are in a second plane; the base member comprises an elevated central portion configured to engage the support member such that the first plane is separated from the second plane by a gap between 1.0 and 4.0 mm; the planar member comprises a central axis at the center of the bearing; a surface of the planar member surrounding each aperture comprises an interface between a cylindrical portion and a tapered conical portion; and a point of the interface that is closest to the central axis is substantially equidistant from the upper planar surface and the lower planar surface a surface of the planar member surrounds each aperture; the surface of the planar member surrounding each aperture comprises the cylindrical portion proximal to the upper planar surface of the planar member; the surface of the planar member surrounding each aperture comprises the tapered conical portion proximal to the lower planar surface of the planar member each aperture in the plurality of apertures comprises a second central axis at the center of the aperture; the surface of the planar member surrounding each aperture comprises an interface between the cylindrical portion and the tapered conical portion; the interface intersects the upper planar surface at a first point and a second point; the second central axis of the aperture extends through the upper planar surface at a third point; the first point, the second point, and the third point are substantially collinear; the device further comprises a control system configured to activate and deactivate each electromagnet in the plurality of electromagnets; the control system is configured to simultaneously activate a number of electromagnets in the plurality of electromagnets, wherein the number of electromagnets simultaneously activated is equal to the number of magnets in the plurality of magnets of the planar member; the control system is configured to sequentially activate and deactivate the plurality of electromagnets in the circle.

8. The device of claim 1 wherein the outer portion of the planar member comprises a plurality of arms extending from the central portion.

9. The device of claim 8 wherein the plurality of arms comprises three arms.

10. The device of claim 8 wherein the support member extends through the bearing positioned in the central portion of the planar member.

11. The device of claim 7 wherein the support member comprises a first portion and a second portion, wherein:
the first portion is configured to couple to the second portion; and
the first portion and the second portion are configured such that the support member extends through the bearing when the first portion is coupled to the second portion.

12. The device of claim 11 wherein the first portion and the second portion are configured to threadably couple to each other.

13. A method of isolating a sample, the method comprising: placing a tubular member in an aperture of the device of claim 1, wherein the tubular member comprises a sample including a liquid comprising macromolecules and a solid; rotating the planar member around the support member; and aspirating a portion of the liquid from the tubular member, wherein: the solid is a magnetic solid and wherein the magnetic solid adsorbs macromolecules and is retained by a magnet when the portion of the liquid is aspirated; wherein the method further comprises, aspirating an initial portion of liquid from the tubular member prior to rotating the planar member around the support member.

14. A device for isolating a sample, the device comprising: a planar member comprising a plurality of sides, an upper planar surface, a lower planar surface, a central portion and an outer portion; a base member; a bearing positioned in the central portion of the planar member; and a support member proximal to the central portion of the planar member, wherein: the bearing comprises a first bearing race and a second bearing race, wherein the first bearing race and the second bearing race are configured to rotate with respect to each other; the planar member is coupled to the first bearing race of the bearing; the support member is coupled to the second bearing race of the bearing; the outer portion of the planar member is coupled to the central portion at each side of the planar member; the outer portion of the planar member is coupled to the central portion at an angle between 125 degrees and 145 degrees; the outer portion comprises a plurality of apertures at each side of the planar member; and the device is configured to allow rotation of the planar member around the support member, wherein: the outer portion comprises eight apertures at each side of the planar member; the base member comprises a plurality of sides equal to the number of sides of the planar member: each side of the base member comprises a plurality of magnets equal to the number of apertures at each side of the planar member; the base member is configured to support the support member, the bearing and the planar member to allow rotation of the planar member with respect to the support member; the plurality of magnets comprises 52 percent Neodymium.

15. A method of isolating a sample, the method comprising: placing a tubular member in an aperture of the device of claim 1, wherein the tubular member comprises a sample including a liquid comprising macromolecules and a solid; rotating the planar member around the support member; and aspirating a portion of the liquid from the tubular member, wherein: the solid is a magnetic solid and wherein the magnetic solid adsorbs macromolecules and is retained by a magnet when the portion of the liquid is aspirated; wherein the method further comprises, aspirating an initial portion of liquid from the tubular member prior to rotating the planar member around the support member.

\* \* \* \* \*